United States Patent
Haubrich et al.

(10) Patent No.: US 6,482,154 B1
(45) Date of Patent: Nov. 19, 2002

(54) LONG RANGE IMPLANTABLE MEDICAL DEVICE TELEMETRY SYSTEM WITH POSITIVE PATIENT IDENTIFICATION

(75) Inventors: Gregory John Haubrich, Champlin, MN (US); Kevin P. Kuehn, Birchwood, MN (US)

(73) Assignee: Medtronic, INC, Minneapolis, MN (US)

(*) Notice: Subject to any disclaimer, the term of this patent is extended or adjusted under 35 U.S.C. 154(b) by 85 days.

(21) Appl. No.: 09/630,999

(22) Filed: Aug. 2, 2000

(51) Int. Cl.[7] ................................................ A61B 5/00
(52) U.S. Cl. ......................... 600/300; 128/903; 607/32
(58) Field of Search ............................... 600/300, 301; 128/897, 898, 899, 903, 904; 607/32, 33, 31

(56) References Cited

U.S. PATENT DOCUMENTS

| | | | | |
|---|---|---|---|---|
| 3,945,387 A | * | 3/1976 | Adams | 607/31 |
| 4,428,378 A | | 1/1984 | Anderson et al. | 128/419 |
| 4,987,897 A | | 1/1991 | Funke | 128/419 |
| 5,052,388 A | | 10/1991 | Sivula et al. | 128/419 |
| 5,113,859 A | | 5/1992 | Funke | 128/419 |
| 5,113,869 A | | 5/1992 | Nappholz et al. | 128/696 |
| 5,404,877 A | | 4/1995 | Nolan et al. | 128/671 |
| 5,499,626 A | * | 3/1996 | Willham et al. | 600/300 |
| 5,855,609 A | * | 1/1999 | Knapp | 128/898 |
| 5,891,180 A | * | 4/1999 | Greeninger et al. | 607/32 |
| 6,009,350 A | | 12/1999 | Renken | 607/32 |

\* cited by examiner

Primary Examiner—Eric F. Winakur
Assistant Examiner—David McCrosky
(74) Attorney, Agent, or Firm—Girma Wolde-Michael; Michael C. Soldner

(57) ABSTRACT

An improved, long range, telemetry system for uplink and downlink telemetry transmission between an implantable medical device (IMD) and an external medical device (EMD), e.g. a programmer or monitor, specifically operable in accordance with a method for ensuring that the telemetry link is between an intended, rather than an un-intended, implantable medical device and the external medical device. Verification is effective if the operator of the EMD observes an implant event signal that is transmitted by uplink telemetry to the EMD from the IMD contemporaneously with a response-provoking action performed in the vicinity of the implant site of the intended patient. The operator directly observes the response-provoking event, when the patient is in sight, or assists the patient in timing the response-provoking event when the patient is not in sight but is at least in voice communication.

29 Claims, 7 Drawing Sheets

LONG RANGE IMPLANTABLE MEDICAL DEVICE TELEMETRY SYSTEM WITH POSITIVE PATIENT IDENTIFICATION

BACKGROUND OF THE INVENTION

The present invention relates generally to telemetry systems for uplink and downlink telemetry transmission between an implantable medical device (IMD) and an external medical device (EMD) such as a programmer or monitor and more specifically to a method for ensuring that the telemetry link is between an intended, rather than an unintended, implantable medical device and the external medical device.

In the context of programming the operating modes or parameters of an IMD or in receiving information from an IMD, it is vital to ensure that programming commands not be received by an IMD other than the device intended to be programmed and that the source of any up-linked information from an IMD is properly identified. In most currently available systems, the programmer must be placed in close proximity to the implanted device, typically by means of a programming head in contact with the patient's body. In such cases, there is little likelihood of confusion as to the identity of the implanted device with which the programmer is communicating.

More recently it has been proposed to provide communication systems for implantable devices in which the programming head is done away with, and communication occurs directly between the implanted medical device and a programmer or monitor which, may be located some distance from the patient. Such systems are disclosed in U.S. Pat. No. 5,404,877 issued to Nolan et al, and U.S. Pat. No. 5,113,869 issued to Nappholz. In the Nappholz patent, in particular, broadcasting RF signals from an implanted device to a programmer or monitor that may be located some feet away from the patient is suggested. Such a communication system is also disclosed in U.S. patent application No. 09/303,178 for a "Telemetry System For Implantable Medical Devices", filed Apr. 30, 1999 by Villaseca et al., which application is incorporated herein by reference in its entirety. In use of such systems, it is possible that multiple patients, each with an implanted device, may simultaneously be within communication range of the associated external device. In such cases, even if a telemetry link is established between the external device and an implanted device, there may still be uncertainty as to which patient's device is communicating with the external device.

SUMMARY OF THE INVENTION

In the context of a telemetry system for communications between an implanted medical device and an associated external medical device located at a distance from the implanted device, the present invention is intended to assure that there is no ambiguity as to which implanted device is communicating with the external device or as to which patient has the device implanted. The invention accomplishes this result by providing a mechanism for indicating which of a number of devices within the communication range of the external device is implanted in a specific patient.

The external device preferably issues a request for communication, which may be received by any of a population of implantable devices that employ the inventive telemetry system. Those devices within range of the external device may in response send a telemetry transmission indicating that the request for communication has been received. This transmission preferably includes an identifier unique to the implanted device. A separate mechanism is provided for activating only the implantable device within a specific patient to send a telemetry transmission including an event signal indicative that the implanted device has been so activated. For example, per the direction of the physician or other individual operating the external device, a magnet may be placed adjacent the device implanted in a specified patient, triggering the uplink transmission of an event signal responsive to the magnet placement. The event signal may also include an identifier unique to the implanted device. The identifier may be used to subsequently communicate only with the device implanted in the specified patient.

If no event signal is received, the device implanted in the specified patient is understood to be either incompatible with the inventive telemetry system or out of range. If the external device receives an up-linked event signal, it is displayed to the operator or triggers a signal indicating its receipt. The operator may then determine whether the received event signal correlates in time to the response-provoking event. If so, the operator can conclude that the device that transmitted the event signal is the device with which communication is desired, and may initiate a telemetry session with that implanted, device. Alternatively, the external device may initiate a telemetry session with an implanted device prior to receipt of an uplink signal from the device, and may use the later uplinked event signal to confirm that communication is underway with the desired implanted device. In such embodiments, receipt of the uplinked event signal may serve as a prerequisite for continuation of the telemetry session and reprogramming of the implanted device.

Other mechanisms for triggering the transmission of the event signal may include, for example, application of pressure to a patient's body, for example by physical impact such as by tapping adjacent the implanted device; audio activation by means of a tone generator, electrical activation by means of an electrical signal applied to the patient's body or activation using an RF signal applied by means other than the remotely located external device.

BRIEF DESCRIPTION OF THE DRAWINGS

The present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS OF THE INVENTION

The present invention relates to a long-range telemetry system of the general type described in the above-referenced Villaseca et al. application wherein an implanted device may be programmed or monitored at a distance from the patient in whom the device is implanted. In an exemplary embodiment, the system may employ RF transmission in an occupied band of about 402–405 MHz as in the Villaseca et al. application. Within this bandwidth, one or a number of communication channels may be available. Other frequency ranges may be substituted. Each telemetry transmission may be formatted in a frame based format using frequency shift keying or other modulation format. Preferably, the effective operating physical distance between the IMD antenna and the external device antenna is at least 2 meters and may be on the order of at 5–10 meters or more.

The IMD may employ for example, an elongated antenna which projects outward from the housing of the IMD, as described in the cited Villaseca et al. application or may employ a coil antenna located external to the device housing as described in U.S. Pat. No. 6,009,350 issued to Renken, incorporated herein by reference in its entirety. The EMD may be equipped with a compatible antenna or set of antennas that are arranged to avoid nulls or dead spots in reception, for example corresponding generally to that disclosed in the above-cited Villaseca et al. application or in U.S patent application No. 09/302,637 for a "Telemetry System For Implantable Medical Devices", filed Apr. 30, 1999 by Geodeke et al., which application is also incorporated herein by reference in its entirety.

Figure 1:
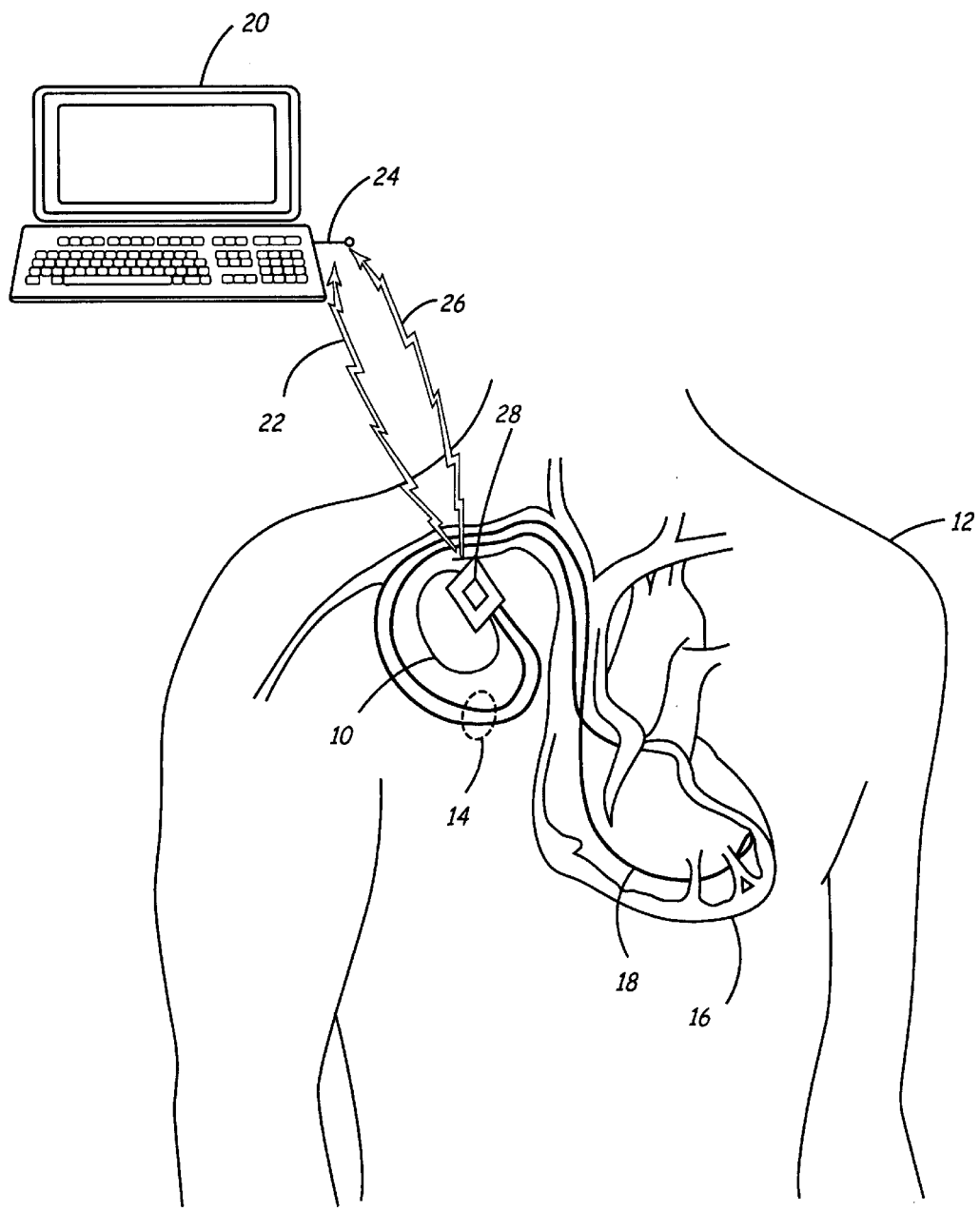
FIG. 1 is a simplified circuit block diagram of major functional uplink and downlink telemetry transmission functions of an exemplary EMD and IMD in accordance with the present invention.

FIG. 1 is a simplified schematic diagram of major functional uplink and downlink telemetry transmission functions allowing bi-directional telemetry communication between an EMD, e.g., an external programmer 20, and an IMD, e.g., a cardiac pacemaker IPG 10, in accordance with the present invention. The IPG 10 is implanted in the patient 12 beneath the patient's skin or muscle and is electrically coupled to the heart 16 of the patient 12 through pace/sense electrodes and lead conductor(s) of at least one cardiac pacing lead 18 in a manner known in the art. The IPG 10 contains an operating system that may employ a microcomputer or a digital state machine for timing sensing and pacing functions in accordance with a programmed operating mode. The IPG 10 also contains sense amplifiers for detecting cardiac signals, patient activity sensors or other physiologic sensors for sensing the need for cardiac output, and pulse generating output circuits for delivering pacing pulses to at least one heart chamber of the heart 16 under control of the operating system in a manner well known in the prior art. The operating system includes memory registers or RAM for storing a variety of programmed-in operating mode and parameter values that are used by the operating system. The memory registers or RAM may also be used for storing data compiled from sensed cardiac activity and/or relating to device operating history or sensed physiologic parameters for telemetry out on receipt of a retrieval or interrogation instruction. All of these functions and operations are well known in the art, and many are employed in other programmable IMDs to store operating commands and data for controlling device operation and for later retrieval to diagnose device function or patient condition.

Programming commands or data are transmitted between an IPG RF telemetry antenna 28 and an external RF telemetry antenna 24 associated with the external programmer 20. In this case, it is not necessary that the external RF telemetry antenna 24 be contained in a programmer RF head of the type described above so that it can be located close to the patient's skin overlying the IPG 10. Instead, the external RF telemetry antenna 24 can be located on the case of the external programmer 20, and the programmer 20 can be located some distance away from the patient 12. For example, the external programmer 20 and external RF telemetry antenna 24 may be on a stand a few meters or so away from the patient 12. Moreover, the patient 12 may be active and could be exercising on a treadmill or the like during an uplink telemetry interrogation of real time ECG or physiologic parameters. The programmer 20 may also be designed to universally program existing IPGs that employ conventional ferrite core, wire coil, RF telemetry antennas of the prior art and therefore also have a conventional programmer RF head and associated software for selective use with such IPGs.

In an uplink telemetry transmission 22, the external RF telemetry antenna 24 operates as a telemetry receiver antenna, and the IPG RF telemetry antenna 28 operates as a telemetry transmitter antenna. Conversely, in a downlink telemetry transmission 26, the external RF telemetry antenna 24 operates as a telemetry transmitter antenna, and the IPG RF telemetry antenna 28 operates as a telemetry receiver antenna. Both RF telemetry antennas are coupled to a transceiver comprising a transmitter and a receiver.

Figure 2:
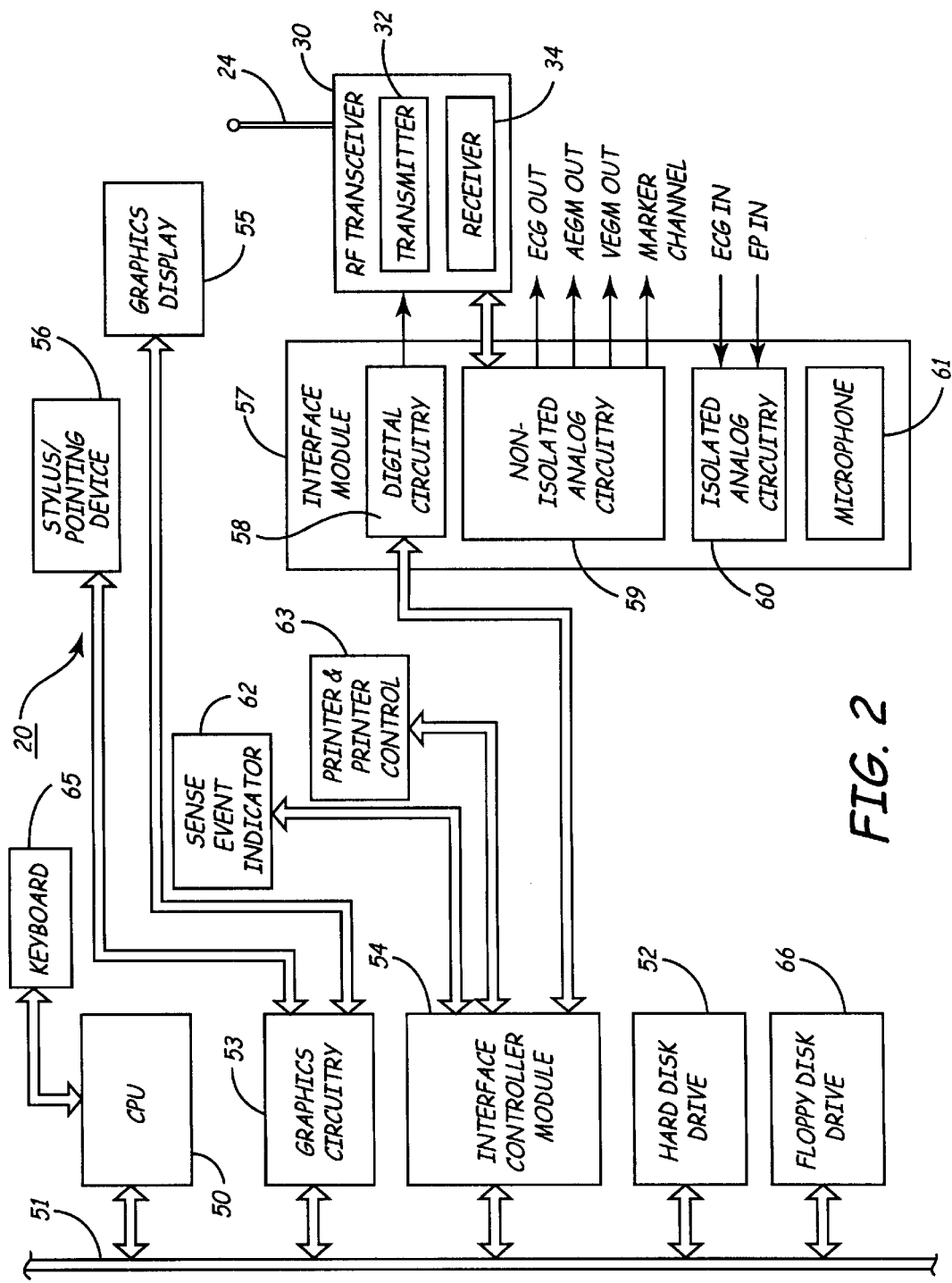
FIG. 2 is a simplified circuit block diagram of major functional blocks of the EMD of FIG. 1

FIG. 2 is a simplified circuit block diagram of major functional blocks of the external programmer 20 of FIG. 1. The external RF telemetry antenna 24 of the programmer 20 is coupled to a telemetry transceiver and antenna driver circuit board 30 including a telemetry transmitter 32 and telemetry receiver 34. The telemetry transmitter 32 and telemetry receiver 34 are coupled to control circuitry and registers operated under the control of a microcomputer and software as described in the above-incorporated, commonly assigned, patents and pending applications. Similarly, within the IPG 10, the IPG RF telemetry antenna 28 is coupled to a telemetry transceiver comprising a telemetry transmitter and telemetry receiver. The telemetry transmitter and telemetry receiver in IPG 10 are coupled to control circuitry and registers operated under the control of a microcomputer and software as described in the above-incorporated, commonly assigned, patents and pending applications.

As shown in FIG. 2, programmer 20 is a personal computer type, microprocessor-based device incorporating a central processing unit 50, which may be, for example, an Intel 80386 or 80486 or Pentium microprocessor or the like. A system bus 51 interconnects CPU 50 with a hard disk drive 52 storing operational programs and data and with a graphics circuit 53 and an interface controller module 54. A floppy disk drive 66 or a CD ROM drive is also coupled to bus 51 and is accessible via a disk insertion slot within the housing of the programmer 20. Programmer 20 further comprises an interface module 57, which includes digital circuit 58, non-isolated analog circuit 59, and isolated analog circuit 60. Digital circuit 58 enables interface module 57 to communicate with interface controller module 54. Operation of the programmer in accordance with the present invention, is controlled by the microprocessor 50, as in turn controlled by software stored on disk drives 52 and/or 66 and/or by EPROM cartridges as described below.

In order for the physician or other caregiver or operator to communicate with the programmer 20, a keyboard 65 coupled to CPU 50 is optionally provided. However the primary communication mode may be through graphics display screen 55 of the well known "touch sensitive" type controlled by graphics circuit 53. A user of programmer 20 may interact therewith through the use of a stylus 56, also coupled to graphics circuit 53, which is used to point to various locations on screen 55 which display menu choices for selection by the user or an alphanumeric keyboard for entering text or numbers and other symbols as shown in the above-incorporated '362 patent. Various touch-screen assemblies are known and commercially available. The display 55 and or the keyboard 65 comprise means for entering command signals from the operator to initiate transmissions of downlink telemetry and to initiate and control telemetry sessions once a telemetry link with an implanted device has been accomplished. Graphics display screen 55 is also used to display patient related data and menu choices and data entry fields used in entering the data in accordance with the present invention as described below. Graphics display screen 55 also displays a variety of screens of telemetered out data or real time data.

Graphics display screen 55 may also display up-linked event signals as that are received and thereby serve as a means for enabling the operator of the programmer to correlate the receipt of uplink telemetry from an implanted device with the response-provoking event to the patient's body as discussed above. Further handshaking functionality may be provided by a device such as microphone 61, which may be used to automatically detect tones generated by the IMD in a manner to be discussed below. Programmer 20 is also provided with a strip chart printer 63 or the like coupled to interface controller module 54 so that a hard copy of a patient's ECG, EGM, marker channel or of graphics displayed on the display screen 55 can be generated.

As will be appreciated by those of ordinary skill in the art, it is often desirable to provide a means for programmer 20 to adapt its mode of operation depending upon the type or generation of implanted medical device to be programmed. Accordingly, it may be desirable to have an expansion cartridge containing EPROMs or the like for storing software programs to control programmer 20 to operate in a particular manner corresponding to a given type or generation of implantable medical device. In addition, in accordance with the present invention, it is desirable to provide the capability through the expansion cartridge or through the floppy disk drive 66 or the CD ROM drive 68 (shown in FIG. 4) to expand or alter the formal generative grammars stored therein or in hard disk drive 52 as experience dictates the need or opportunity to do so.

The non-isolated analog circuit 59 and the digital circuitry 58 of interface module 57 is coupled to the transceiver and antenna driver circuit board 30 which is used to establish the uplink and downlink telemetry links between the IPG 10 and programmer 20 as described above. The atrial and ventricular sense amp circuits of IPG 10 may also be provided with (electrogram) EGM amplifiers that produce atrial and ventricular EGM signals. These A EGM and V EGM signals may be digitized and uplink telemetered to programmer 20 on receipt of a suitable interrogation command. The uplink telemetered EGM signals are received in programming head 22 and provided to non-isolated analog circuit 59. Non-isolated analog circuit 59, in turn, converts the digitized EGM signals to analog EGM signals (as with a digital-to-analog converter, for example) and presents these signals on output lines designated in FIG. 4 as A EGM OUT and V EGM OUT. These output lines may then be applied to a stripchart recorder 63 to provide a hard-copy printout of the A EGM or V EGM signals transmitted from IPG 10 for viewing by the physician. As these signals are ultimately derived from the intracardiac electrodes, they often provide different information that may not be available in conventional surface ECG signals derived from skin electrodes.

IPG 10 may also be capable of generating so-called marker codes indicative of different cardiac events that it detects. A pacemaker with markerchannel capability is described, for example, in U.S. Pat. No. 4,374,382 to Markowitz, which patent is hereby incorporated by reference herein in its entirety. The markers provided by IPG 10 may be received by programming head 22 and presented on the MARKER CHANNEL output line from non-isolated analog circuit 59.

Isolated analog circuit 60 in interface module 57 is provided to receive external ECG and electrophysiological (EP) stimulation pulse signals. In particular, analog circuit 60 receives ECG signals from patient skin electrodes and processes these signals before providing them to the remainder of the programmer system in a manner well known in the art. Circuit 60 further operates to receive the EP stimulation pulses from an external EP stimulator for the purposes of non-invasive EP studies, as is also known in the art.

In accordance with the present invention, the programmer 20 is operated following the steps set forth in FIGS. 6 and 7 and described below to downlink transmit a beacon or "EMD discovery" signal that is received by any IMD, e.g. IPG 10 in FIG. 1, in range of the downlink transmission 26. Each such IMD, including IPG 10, responds with an uplink telemetry transmission, e.g., uplink telemetry transmission 22 in FIG. 1, of an ID or "IMD discovery" signal. Then, a response-provoking event is performed in the vicinity of the IMD by the patient or another person to cause the intended IMD, e.g., IPG 10, to transmit an event signal via an uplink telemetry transmission that is received in receiver 34, processed in interface module 57 and transmitted through the interface controller module 54 to the CPU 50. The event signal is then displayed on the programmer graphics display screen 55 and/or may indicated audibly or visibly by a separate event indicator 62. The operator of programmer 20 either directly observes the response-provoking event when the patient is in sight, or assists the patient in timing the response-provoking event when the patient is not in sight but is at least in voice communication. If the operator of the EMD observes an event signal that is transmitted by uplink telemetry to the EMD from the IMD contemporaneously with a response-provoking event performed adjacent the IMD of the intended patient, he or she then enters verification via the keyboard 65 or stylus pointing device 56, in turn triggering a downlink transmission to the implanted device from which the event signal was received, requesting initiation of a telemetry session or allowing continuation of a previously initiated telemetry session.

Figure 3:
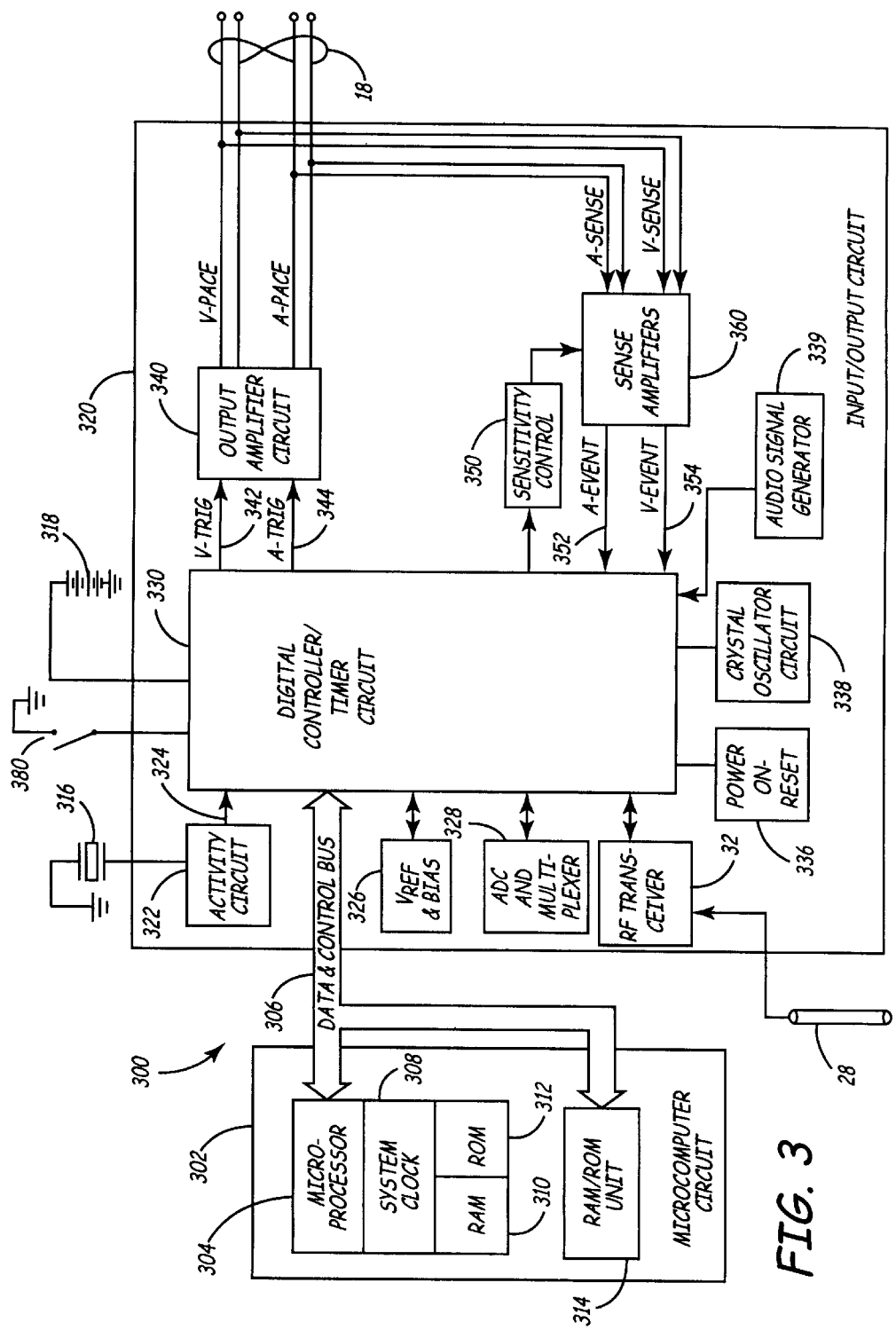
FIG. 3 is a simplified circuit block diagram of major functional blocks of the IMD of FIG. 1

FIG. 3 is a simplified circuit block diagram 300 of major functional blocks of the IPG 10 of FIG. 1, which is an example of an IMD in which the present invention may be practiced. In the block diagram 300, there are at least two alternative sensors described below that are capable of responding to a response-provoking event by providing a detection signal that is processed and then converted to a EMD discovery signal that is transmitted in an uplink telemetry transmission 22 (FIG. 1). Uplink and downlink telemetry transmissions 22 and 26 are effected by the telemetry transceiver and antenna driver circuit board 332 that includes a telemetry transmitter and a telemetry receiver coupled with the IPG RF telemetry antenna 28. The telemetry transmitter and telemetry receiver are coupled to control circuitry and registers for compiling data and signals for uplink telemetry transmissions and for storing and decoding requests and commands embedded in downlink telemetry transmissions. The microcomputer 302 also stores and carries out the protocol governing the formatting of uplink telemetry transmissions and the timing and steps of carrying out the telemetry session protocols.

The IPG block diagram 300 is divided generally into a microcomputer circuit 302, an input/output circuit 320, and peripheral components including connectors for atrial and ventricular leads 18, the IPG RF telemetry antenna 28, a battery 318, an activity sensor 316 responsive to application of pressure and a magnetic field responsive solid state or reed switch 380. The block diagram 300 is fairly typical of prior art dual chamber pacemaker IPG circuits except for the specific configuration of the RF telemetry antenna, the transceiver 332 and the operating software for practicing the steps of the present invention.

The input/output circuit 320 includes a digital controller/timer circuit 330 coupled with a pulse generator output amplifier circuit 340, sense amplifiers 360, the IPG RF transceiver 332, other circuits and inputs described below and with a data and control bus 306 for communicating with the microcomputer circuit 302. The pulse generator circuit 340 includes a ventricular pulse generator circuit and an atrial pulse generator circuit, and The sense amplifier circuit 360 includes atrial and ventricular sense amplifiers adapted to coupled to the atrium and ventricle of the patient's heart by means of leads 14. The output circuit 340 and sense amplifier circuit 360 may contain pulse generators and sense amplifiers corresponding to any of those presently employed in commercially marketed cardiac pacemakers.

Crystal oscillator circuit 338 provides the basic timing clock for the circuit, while battery 318 provides power. Power on reset circuit 336 responds to initial connection of the circuit to the battery for defining an initial operating condition and similarly, resets the operative state of the device in response to detection of a low battery condition. Reference and bias circuit 326 generates stable voltage reference and currents for the analog circuits within the input/output circuit 320. Analog to digital converter ADC and multiplexor circuit 328 digitizes analog signals and voltage to provide real time telemetry if a cardiac signals from sense amplifiers 360, for uplink transmission via RF transceiver circuit 332. Voltage reference and bias circuit 326, ADC and multiplexor 328, power on reset circuit 336 and crystal oscillator circuit 338 may correspond to any of those presently used in current marketed implantable cardiac pacemakers. Audio Signal Generator 339 may be provided to generate audible tones in response to telemetry downlink sessions initiated by the EMD, as discussed below.

Control of timing and other functions within the pacemaker circuit is provided by digital controller/timer circuit 330, which includes a set of timers and associated logic. Digital controller/timer circuit 330 defines the basic pacing interval of the IPG 10, which may take the form of an A—A escape interval initiated on atrial sensing or pacing and triggering atrial pacing at the expiration thereof or may take the form of a V—V escape interval, initiated on ventricular sensing or pacing and triggering ventricular pulse pacing at the expiration thereof. Digital controller/timer circuit 330 similarly defines the A-V escape intervals SAV and PAV. The microcomputer circuit 302 via data and control bus 306 controls the specific values of the intervals defined. Sensed atrial depolarizations are communicated to the digital controller/timer circuit 330 on A event line 352, with ventricular depolarizations communicated to the digital controller/timer circuit 330 on V event line 354. In order to trigger generation of a ventricular pacing pulse, digital controller/timer circuit 330 generates a trigger signal on V trigger line 342. Similarly, in order to trigger an atrial pacing pulse, digital controller/timer circuit 330 generates a trigger pulse on a trigger line 344.

Digital controller/timer circuit 330 also defines time intervals for controlling operation of the sense amplifiers in sense amplifier circuit 360. Typically, digital controller/timer circuit 330 will define an atrial blanking interval following delivery of an atrial pacing pulse, during which atrial sensing is disabled, as well as ventricular blanking intervals following atrial and ventricular pacing pulse delivery, during which ventricular sensing is disabled. Digital controller/timer circuit 330 will also define an atrial refractory period during which atrial sensing is disabled, this refractory period extending from the beginning of the A-V escape interval following either a sensed or paced atrial depolarization, and extending until a predetermined time following sensing of a ventricular depolarization or delivery of a ventricular pacing pulse. Digital controller/timer circuit 330 similarly defines a ventricular refractory period following ventricular sensing or delivery of a ventricular pacing pulse, which is typically shorter than the portion of the atrial refractory period following ventricular sensing or pacing. Digital controller/timer circuit 330 also controls sensitivity settings of the sense amplifiers 360 by means of sensitivity control 350.

Microcomputer circuit 302 controls the operational functions of digital controller/timer 324, specifying which timing intervals are employed, and controlling the duration of the various timing intervals, via data and control bus 306. Microcomputer circuitry contains a microprocessor 304 and associated system clock 308 and on processor RAM circuits 310 and 312, respectively. In addition, microcomputer circuit 302 includes a separate RAM/ROM chip 314. Microprocessor 304 is interrupt driven, operating in a reduced power consumption mode normally, and awakened in response to defined interrupt events, which may include delivery of atrial and ventricular pacing pulses as well as sensed atrial and ventricular depolarizations. In addition, if the device operates as a rate responsive pacemaker, a timed interrupt, e.g., every two seconds, may be provided in order to allow the microprocessor to analyze the output of the activity circuit 322 and update the basic rate interval (A—A or V—V) of the device. In addition, the microprocessor 304 may also serve to define fixed or variable A-V escape intervals and atrial and ventricular refractory periods which may also decrease in duration along with decreases in duration of the basic rate interval. Similarly microprocessor 304 may define atrial and/or ventricular refractory periods which decrease in duration as a function of sensed or paced heart rate.

In FIG. 3, the IPG 10 is provided with the piezoelectric activity sensor 316, which is intended to monitor patient activity, in order to allow provision of rate responsive pacing, such that the defined pacing rate (A—A escape interval or V—V escape interval) increases with increased demand for oxygenated blood. Activity sensor 316 is typically mounted inside and against the IPG housing and is responsive to pressure waves or shocks transmitted to it through the patient's body. Activity sensor 316 normally generates electrical signals in response to sensed physical activity, namely shocks transmitted through the body from patient foot steps while walking or running, which are processed by activity circuit 322 and provided to digital controller/timer circuit 330. Activity circuit 332 and associated sensor 316 may correspond to the circuitry disclosed in U.S. Pat. No. 5,052,388, issued to Betzold et al., and U.S. Pat. No. 4,428,378, issued to Anderson et al. incorporated herein by reference in their entireties. In normal use, the activity circuit 322 operates in conjunction with software algorithms and programmed signal processing values in microcomputer 302 to derive an activity signal correlated to rate at which footsteps are sensed and to then adjust the pacing lower rate to the sensed patient activity level.

Figure 4:
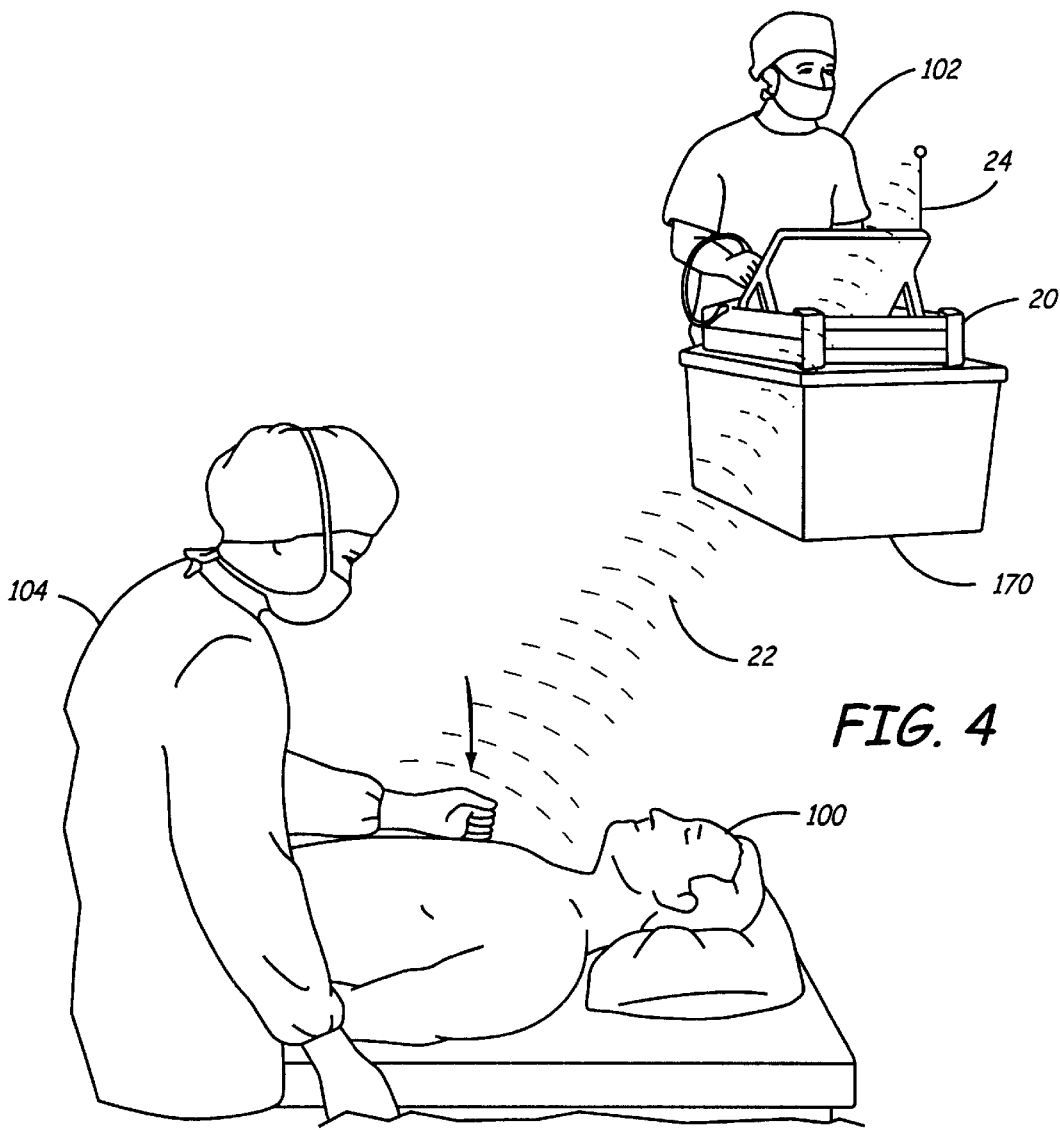
FIG. 4 is a simplified schematic illustration of a long range telemetry system for programming an IMD in a clinical setting in accordance with a first embodiment of a system according to the present invention.

In one embodiment of the present invention illustrated in FIG. 4, the activity circuit 322 and activity sensor 316 of IPG 10 (or other IMD) may be used while the patient 100 is at rest to generate the implant event signal. After the IPG is placed in the ready state as described above, tapping the patient's skin over the implant site by the assistant 104 or the patient causes the activity sensor 316 to generate a sensor output signal which, in this context, is processed by activity circuit 322 and within digital controller/timer circuit 330 to develop the EMD discovery signal that is then encoded and transmitted via RF transceiver 332 and IPG RF antenna 28 in an uplink telemetry transmission 22. The operator 102 observes the delivery of the tapping by the assistant 104 and the contemporaneous display of the implant event signal on the graphics display screen and/or sense event indicator 62 of the programmer 20 located at the somewhat remote station 170. It is simply necessary that the patient 100 remain seated or reclining during this initial verification phase prior to the commencement of the telemetry session. During the succeeding telemetry session, following verification, the patient 100 can be instructed to exercise to test the rate responsive operating mode and program differing rate control parameters and values. This technique, and these components, can be incorporated into other IMDs than rate responsive pacemakers and may be employed with other EMDs than the programmer 20, e.g., a bedside monitor for home use as illustrated in FIG. 7 described below or in clinical use, or in the context of re-programming an IMD in an office visit.

In FIG. 3, the IPG 10 is also provided with a solid state or reed switch 380 that is either opened or closed in response to an externally applied magnetic field. Conventionally, the magnetic field responsive switch 380 is employed to respond to the magnet in a conventional RF programming head for enabling the above-described closely coupled telemetry transmissions. The magnetic field responsive switch 380 in some embodiments of the present invention may be employed to initiate transmission of an event signal if activated by a magnetic field applied to the patient's body while the implanted device is in the ready state. In such embodiments the magnetic field responsive switch 380 may also be used to initially enable or "wake-up" the receiver in the IMD or to increase its polling frequency.

Figure 5:
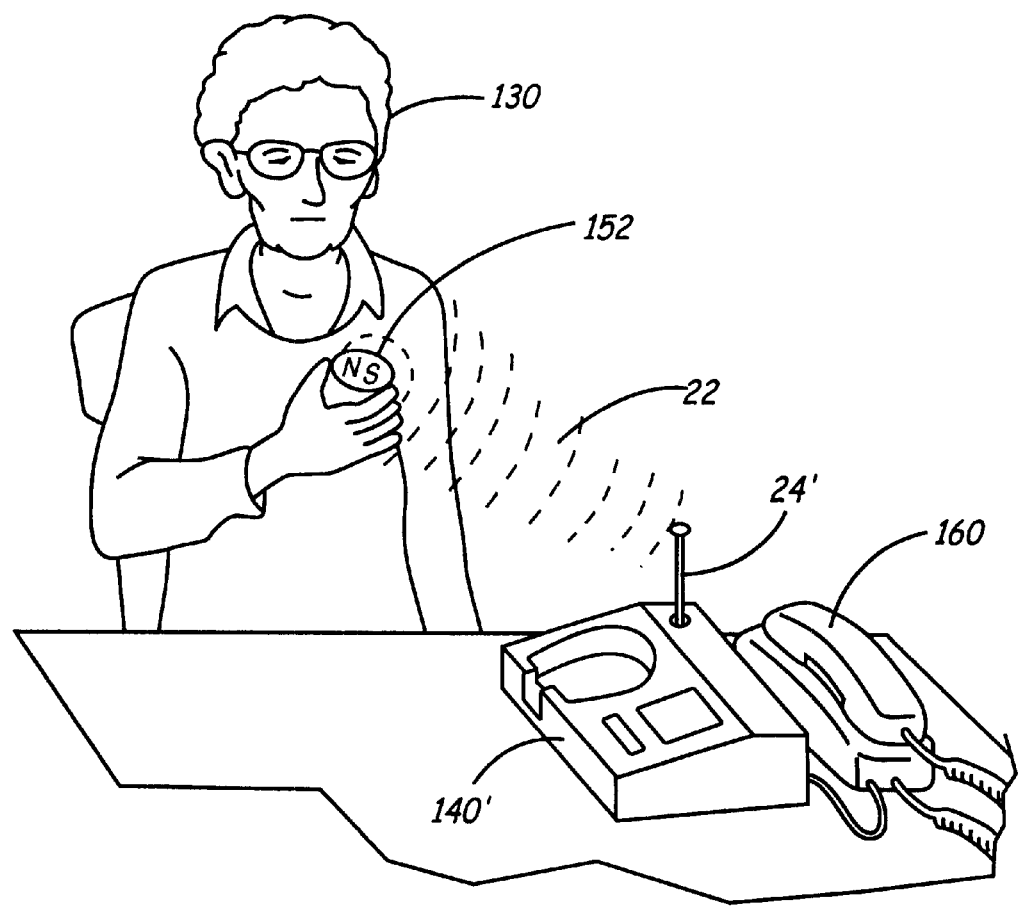
FIG. 5 is a simplified schematic illustration of a long range telemetry system for monitoring the operation of an IMD with a home based monitor in accordance with a second embodiment of a system according to the present invention.

In the embodiment of the present invention illustrated in FIG. 5 in the context of a home based telephone monitor 140, the magnetic field responsive switch 380 of IPG 10 (or other IMD) may be used while the patient 130 is at rest to trigger transmission of the event signal. After the IPG 10 (or other IMD) is placed in the ready state as described above, a magnet 152 applied to the patient's skin over the implant site causes the switch 380 to open or close and to generate a switch output signal. In this context, the switch output signal is processed by digital controller/timer circuit 330 to develop the event signal that is then encoded and transmitted via RF transceiver 332 and IPG RF antenna 28 in an uplink telemetry transmission 22 to the monitor 140'. It is simply necessary that the patient 130 remains still and holds the magnet 152 close to the skin during this initial verification phase prior to the commencement of the telemetry session. In the particular environment in which this second embodiment is illustrated, the remote operator may have to orally instruct the patient 130 when to apply and remove the magnet 152 while he or she observes the remote monitor graphics display screen and/or the sense event indicator. During the actual telemetry session, following verification, the patient can be instructed to remove the magnet 152. This technique, and these components, can be incorporated into other IMDs than pacemakers and may be employed with other EMDs than the monitor 140', e.g., a bedside monitor for clinical use or in the programming context illustrated in FIG. 4 or in a re-programming context in an office visit.

The illustrated circuitry of FIGS. 2 and 3 is merely exemplary, and corresponds to the general functional organization of microcomputer controlled programmers and IMDs presently commercially available. It is believed that the present invention is most readily practiced in the context of such IMDs and EMDs, and that the present invention can therefore readily be practiced using software algorithms stored in RAM or ROM associated with the microcomputers. However, the present invention may also be usefully practiced by means of full custom integrated circuits, for example, a circuit taking the form of a state machine, in which a state counter serves to control an arithmetic logic unit to perform calculations according to a prescribed sequence of counter controlled steps. As such, the present invention should not be understood to be limited to a programmer and an IPG having an architecture as illustrated in FIGS. 2 and 3, and a circuit architecture as illustrated in FIGS. 2 and 3 is not believed to be a prerequisite to enjoying the benefits of the present invention.

In a still further embodiment of the present invention, the patient 130 in the illustration of FIG. 5 or the assistant 104 in the illustration of FIG. 4 may be provided with a remote module containing a low power transceiver and power supply for effecting a downlink telemetry transmission of a response-provoking event signal on command from the operator. In this embodiment, the remote module is triggered by the patient or the assistant, while the operator observes the event directly or indirectly and the corresponding implant event signal. The downlink telemetry transmission from the remote module can be encoded so that only the IMD can recognize and decode the response-provoking event signal. In other embodiments of the invention, the implanted device may be provided with any of a variety of sensors capable of responding to stimuli or signals applied to the patient's body to trigger uplink transmission of an event signal, including audio sensors, light sensors, pressure sensors, and sensors of electrical signals transmitted using the patient's body as a conductor, for example as disclosed in U.S. Pat. No. 5,113,859, issued to Funke or U.S. Pat. No. 4,987,897, also issued to Funke, both also incorporated herein by reference in their entireties.

Figure 6:
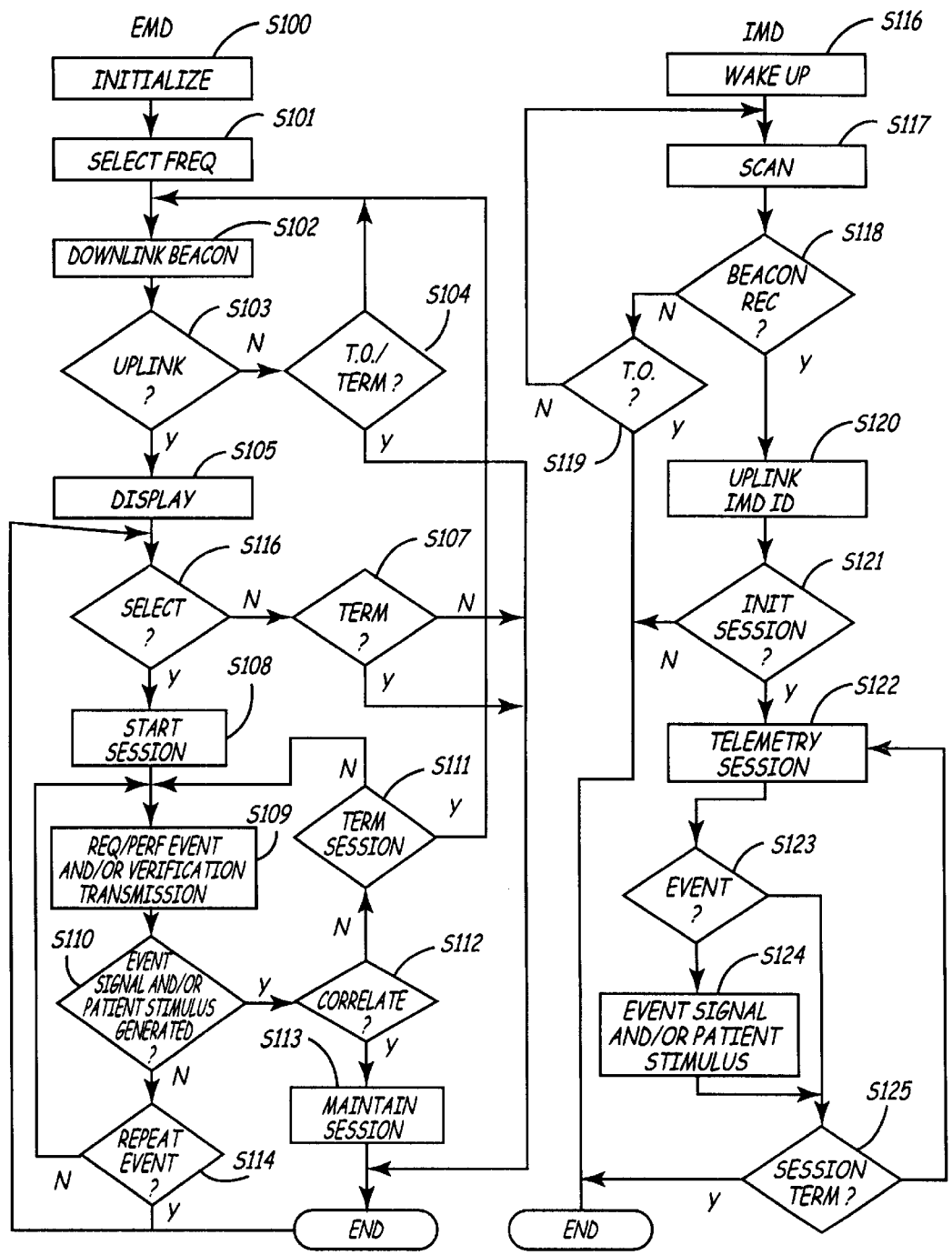
FIG. 6 includes a pair of flow charts illustrating the method of operation of a first preferred embodiment of a system according to the present invention.
Figure 7:
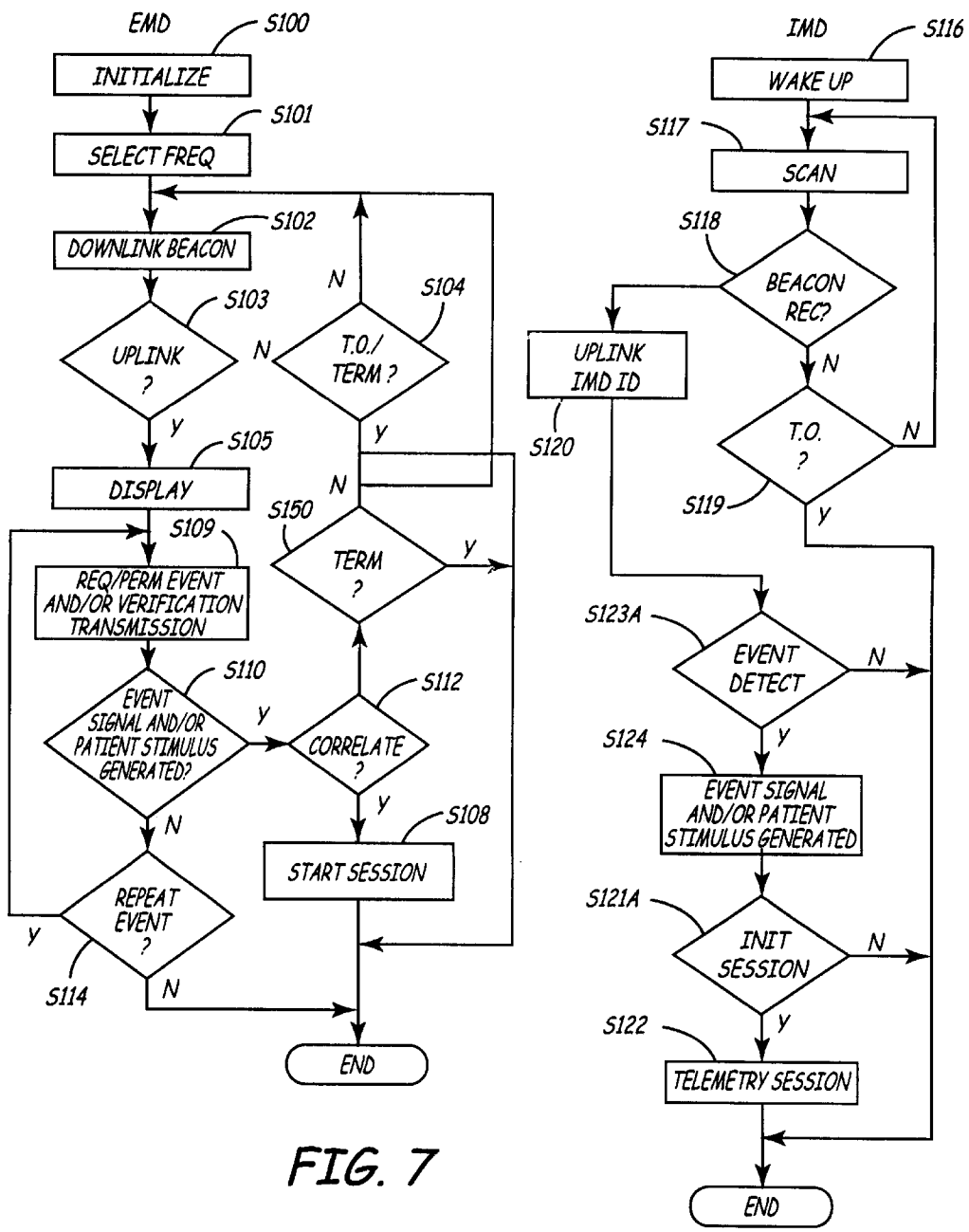
FIG. 7 includes a pair of flow charts illustrating the method of operation of a second preferred embodiment of a system according to the present invention.

FIGS. 6 and 7 each take the form of a pair of functional flow charts illustrating the operation of both the EMD and the IMD in conjunction with the present invention. It should be understood that operation of the IMD and EMD according to these flow charts as illustrated takes place concurrently. FIG. 6 illustrates an embodiment of the invention in which correlation between the response-provoking event and the up-linked event signal is employed to verify that a previously initiated telemetry session is occurring between the EMD and the IMD of interest, for example as a prerequisite to continuation of the telemetry session or as a prerequisite to re-programming the IMD. FIG. 7 illustrates an embodiment of the invention in which the correlation between the response-provoking event and the uplinked event signal is employed as a prerequisite to initiation of a telemetry session. In both flow charts, the functional steps illustrated may be performed by the EMD, the EMD operator or the IMD, as described below.

FIG. 6 illustrates the operation of a first embodiment of the present invention for assuring positive patient identification in either the clinical or surgical setting of FIG. 4, for example, or in the remote home setting of FIG. 5. In the former case, there is a possibility that the use of the EMD, e.g. a programmer or monitor, may result in eliciting a response from an unintended IMD within telemetry range. In the latter case, the remote operator needs to be assured that communication is taking place only with the medical device implanted in the patient of interest at the other end of the telephone connection rather than an IMD implanted in another patient that might happen to be in the range of the telephone monitor or programmer. The interactive method and system implementing the method requires that the medical personnel operating the EMD at a distance from the patient of interest can directly or indirectly observe the response-provoking event intended to trigger transmission of the event signal.

The steps of FIG. 6 will first be explained in relation to the scenario illustrated in FIG. 4 where the operator of the EMD, e.g. a programmer 20, can observe the patient at a distance from the programmer. In step S100, the operator of the EMD triggers initialization using an appropriate input device of the EMD, causing the EMD to initialize its hardware and software in anticipation of commencing a telemetry session. The EMD is provided with software employed by its CPU to initialize its telemetry transmission system for communicating with a variety of IMDs and to provide for display of the range of programmable operating mode and parameter values or data fields that may be interrogated and that are appropriate to the particular implanted device. The operator 102 may need to know at least the type of IMD that is implanted in the patient 100. For example, the operator 102 may select the general type of IMD to be interrogated or programmed from a displayed menu and then follow a series of displayed questions and instructions making appropriate keyboard or touch screen entries that serve to identify at least the manufacturer or the manufacturer and model of IMD.

When the selection is completed to the extent possible, the EMD 20 may, if so configured, enter a channel scan mode at S101 wherein an available, un-occupied, communication channel in the operating frequency range is selected, in a fashion analogous to the operation of multi-channel cordless phones. Alternatively, the operator may select a communication channel or the EMD may be hardware-limited to a single communication channel.

If the IMD has a telemetry system that is not continuously activated, the telemetry system of the IMD with which communication is desired may be activated at S116, for example by application of a magnet to the device. Alternatively, the IMD may be configured to automatically activate its receiver intermittently. Once activated, the IMD may then sequentially scan available communication channels at S117 until expiration of a defined time period at S119 or receipt of a beacon or EMD discovery downlink signal at S118. In single channel embodiments the IMD may simply await receipt of a beacon signal without scanning.

In step S102, the operator 102 enters a command on the EMD display or keyboard, and the EMD (programmer 20) transmits a beacon or EMD discovery signal via downlink telemetry and waits for a predetermined time for receipt of an uplinked IMD discovery or ID signal at S103. If no uplinked signal is received, multiple re-transmissions of the EMD discovery signal may optionally be triggered, continuing until terminated by the operator or until expiration of a defined time period at S104.

If the EMD discovery or beacon signal is received by an IMD or IMDs within communication range of the EMD in step S118, the IMDs transmit their ID codes or other IMD discovery signals via uplink telemetry at S120 using the same channel as employed by the EMD for downlink telemetry. In order that IMD discovery signals from more than one IMD can be accurately detected, it is preferable that the IMD discovery signals from the IMDs are generated by their transceiver circuitry (e.g. transmitter/receiver 332, FIG. 3) at staggered time intervals, with the time durations of the intervals varied by the IMDs to prevent repeated overlapping transmission of IMD discovery signals from multiple IMDs. To accomplish this result, individual IMDs may be provided with hardware or software defined intervals separating transmissions of IMD discovery signals from previously received EMD discovery signals, which differ from device to device. Alternatively, each IMD may be provided with programming allowing the microprocessor 304 (FIG. 3) to define randomly variable time intervals between received EMD discovery signals and transmissions of IMD discovery signals. In addition to triggering uplink transmission of the IMD discovery signal, the EMD discovery signal places the IMD or IMDs in a ready state during which the IMD waits for occurrence of a response-provoking event such as application of a magnet, physical impact, or the like, as described below. The IMD in this embodiment also awaits initiation of a telemetry session by the EMD at S121 for a predetermined time period. If no telemetry session is initiated, the IMD may terminate the attempt to establish communication at S126.

If no IMD discovery signals are received by the EMD at S103 within a defined time period following transmission of the EMD discovery signal at S102, the operator of the EMD may terminate the attempt to establish a telemetry link at S104. Alternatively, the EMD may repeat the transmission of the beacon or EMD discovery signals at S102 until expiration of a longer time-out period at S104. The EMD displays at S105 all IMD discovery signals that may be elicited by the EMD discovery signal, including any. identifying data relative to the IMDs which transmitted the IMD discovery signals. The operator may then select a desired one of the IMDs having signals displayed at S106. If none of the IMDs having displayed signals are the IMD of interest to the operator, the operator may terminate the attempt to establish communication at S107 or trigger a repeat of the beacon or EMD discovery signal at S102.

Following selection of an IMD at S106, the EMD initiates a telemetry session with the selected IMD at S108, by means of a downlink telemetry transmission to the selected IMD at S122. In one embodiment, the initiation of a telemetry session could include the generation by the IMD of some type of patient stimuli to provide notification of the initiated session. This could include an audible signal, a vibration, a pacing rate shift, a pacing burst, or any other type of stimuli that is detectible by the patient so that the patient and/or an assisting operator is notified of the session.

In some embodiments of the invention, bi-directional communication between the IMD and EMD may now begin, including transmissions, for example, of preliminary information regarding device status from the IMD to the EMD.

At S109, the operator of the EMD requests that an assistant or the patient perform a response-provoking event in the region of the implant site that is detectable by the IMD. For example a magnet may be applied to the patient's skin over the IMD that closes a reed switch. Alternatively, the patient's skin over the IMD may be tapped to create a signal detectable by a pressure or activity sensor as described above. Normally, such an event would not trigger an uplink telemetry transmission, but the ready state enables the IMD to respond by transmitting an event signal to the EMD at S124, as discussed above. If an event signal is generated at S110, the event signal may be displayed and stored by the EMD. For example, this event signal could cause the EMD to highlight the identification signals of the device providing the event signal on an EMD screen. This allows the operator to verify that the telemetry session has been initiated with the correct device. The event signal may also include identifying information that may be used by the EMD in subsequent telemetry transmissions to the IMD to assure that only the desired IMD receives and responds to transmissions from the EMD.

If the IMD does not detect a response-provoking event at S123, it continues the telemetry session until terminated by the EMD at S125.

In one embodiment, the operator may have the option to initiate a verification transmission to the selected device. Alternatively, this initiation of a verification transmission could be performed automatically by the EMD. This could be done after generation of the response-provoking event discussed above, or instead of using the response-provoking event. According to this option, a device is selected to be the target of a telemetry transmission. When the IMD receives this transmission, the IMD responds by generating some type of patient stimulus. This stimulus could include an audible signal, a vibration, a pacing rate shift or a pacing burst that is detectable by EKG electrodes, or any other type of stimulus that is detectible by the patient and/or the assisting operator so that the assisting operator is further able to verify that the telemetry session has been initiated with the correct device.

In one embodiment wherein patient stimulus is generated in response to the response-provoking event, the EMD could automatically detect this response-provoking event. This detection could be used by the EMD as a prerequisite for continuing the telemetry session. For example, an audible tone generated by the IMD could be detected by microphone 61 within EMD, and used to verify that the telemetry session has been initiated with the correct device. In another embodiment, a unique waveform pulse could be generated by the IMD that is detectable by an EKG electrode coupled to EMD.

Following transmission of the event signal and/or generation of the patient stimulus at S124, the IMD awaits further communications as part of the ongoing telemetry session or a communication terminating the telemetry session at S125.

If no up-linked event signal and/or patient stimulus is generated at S110, the operator may elect at S114 to terminate the telemetry session at S114 resulting in a downlink transmission to the IMD ending the telemetry session. If the operator does not wish to terminate the session at S114, the request for and performance of the response-provoking event at S109 may be repeated.

If an up-linked event signal and/or patient stimulus is generated by the IMD and detected by the EMD, the signals received by the EMD are decoded and displayed and/or signaled by the EMD at S110. The operator 102 of the EMD observes at S112 the correlation or lack of correlation between the response-provoking event, any patient stimulus, and the display of the corresponding received event signal. Preferably, the operator enters a confirmation of the observed correlation if an event signal is displayed contemporaneously with or immediately following the observed response-provoking event at S112, enabling continuation of the telemetry session at S113. S113. As discussed above, the operator may further confirm this correlation by noting any patient stimuli generated by the IMD following a specific telemetry transmission by the EMD. Reprogramming of the IMD parameters may then be accomplished with certainty that the IMD of interest is the IMD in communication with the EMD. The telemetry session is continued at S13 until terminated by the operator.

If no correlation is observed, the operator may terminate the telemetry session at S111 or alternatively the EMD may automatically do so, resulting in a downlink transmission to the IMD ending the telemetry session. The EMD may then send new beacon signals at S102 as illustrated, to again attempt to contact the IMD of interest. If the operator or the EMD does not terminate the session at S111, the request for and performance of the response-provoking event at S109 may optionally be repeated. In alternative embodiments, the operator or the EMD may instead select a different IMD at S106 or terminate the attempt to establish communication at S107.

By means of a received up-linked event signal correlated to the response-provoking event, the operator 102 is assured that communication is occurring with the IMD in the desired patient 100 and not with some other IMD in another patient within the telemetry range. In the event of a failure to establish a telemetry link with the IMD of interest, the process illustrated in FIG. 6 may be repeated, perhaps after moving the patient 100 or the EMD station 170.

In the course of a telemetry session, the EMD transmits interrogation or programming commands by downlink telemetry that are received and acted upon by the IMD in real time. Typically, the IMD then transmits requested data and/or confirmation of programming after a prescribed delay by uplink telemetry to the external device. The human operator, of the external programmer or monitor can then decide to transmit further commands via downlink telemetry as desired.

The method illustrated in FIG. 6 can be modified and employed in the context of monitoring or programming in IMD in a patient 130 who is not visable to the operator of the programmer and is accessed by telephone or through another voice link as illustrated in FIG. 5. In this case, the patient 130 may be instructed to perform the response-provoking event in conjunction with a countdown voiced by the remote operator or while the patient says "applied" simultaneously with the performance of the response-provoking event. The remote operator can then observe the correlation of lack thereof as S112. It should also be understood that the method of the present invention may be implemented in other settings including the monitoring of patients recuperating in a hospital or clinic. If programming or monitoring is accomplished with the patient in close proximity to the programmer, the EMD operator may of course simply perform the response-provoking event at S109.

As discussed above, the embodiment of FIG. 7 employs correlation between the uplinked event signal and the response-provoking event as a prerequisite to initiation of a telemetry session as opposed to being a prerequisite to continuation of a telemetry session or as a prerequisite it reprogramming of the IMD. In this context, the functional steps employed in the embodiment of FIG. 7 include many of those employed in FIG. 6, but occur in different order and relationship to one another. Steps in FIG. 7 are numbered according to the corresponding steps in FIG. 6.

The EMD is initialized, selects a frequency if necessary and sends beacon signals until receipt of an uplinked IMD discovery or ID signal or termination at steps S101–S104, precisely as in FIG. 6. Similarly, the IMD is awakened, if necessary scans for a beacon signal at steps S116–S119 and enters a ready state during which it awaits the occurrence of a response-provoking event at S123A. The IMD transmits an IMD discovery signal at S120, which is received and displayed at S105 also as described above in conjunction with FIG. 6. Unlike the embodiment of FIG. 6, the IMD also preferably sets a maximum time interval or ready period following receipt of a beacon signal during which a response-provoking event may be detected at S123A. Failure to detect a response-provoking event prior to termination of the ready period at S123A results in the IMD exiting the ready state and terminating the attempt to establish a communication link with the EMD, until receipt of a subsequent beacon or EMD discovery signal.

After receipt of the IMD discovery or ID signals at S105, the EMD does not allow for selection of an IMD and immediate initiation of a telemetry session as in FIG. 6. Instead, the EMD operator proceeds directly to request or perform the response provoking event at S109, as discussed above in conjunction with FIG. 6. In response to detection of the response-provoking event within the ready period at S123A, the IMD uplinks an event signal at S124, also as described in conjunction with FIG. 6. Rather than awaiting initiation of a telemetry session following the received beacon signal as in FIG. 6, the IMD now awaits initiation of a telemetry session at S121A for a defined time period following receipt of the beacon signal at S118 or for a defined time period following detection of the response-provoking event at S123A. Failure to initiate a telemetry session within the defined time period results in termination of the attempt to establish a communication link with the IMD.

Following response provoking event at S109, the EMD waits for a defined time period for receipt of an uplinked event signal at S110, as in FIG. 6. Following failure to receive the event signal, during this time period at S100, the EMD operator may elect at S114 to terminate the attempt to establish communication with the IMD or may repeat the response-provoking event at S109, also as described in FIG. 6.

If an event signal is received at S110, the EMD operator observes whether the event signal correlates with the response-provoking event at S112, as in FIG. 6. If the event signal correlates with the response-provoking event, the EMD operator may initiate or the EMD may automatically initiate a telemetry session at S108, as in FIG. 6. In response to receipt of a signal from the EMD at S121A, The IMD enters the telemetry session at S122, where it remains until the session is terminated by the EMD. In the event that correlation is not observed at S112, the operator or the EMD may determine at S150 whether to initiate retransmission of the beacon signals at S102 or to simply terminate the attempt to establish a communications link with the IMD of interest. In alternative embodiments, the EMD operator or the EMD may instead elect to repeat the response-provoking event at S109.

The preceding specific embodiments are illustrative of the practice of the invention. It is to be understood, therefore, that other expedients known to those of skill in the art or disclosed herein may be employed without departing from the invention or the scope of the appended claims. It is therefore to be understood, that within the scope of the appended claims, the invention may be practiced otherwise than as specifically described without actually departing from the spirit and scope of the present invention.

What is claimed is:

1. A medical device system, comprising:
an external medical device generating downlink telemetry transmissions to and receiving uplink telemetry transmissions from a plurality of implantable medical devices, the external medical device simultaneously transmitting a first signal to a plurality of implantable medical devices; and
a transceiver, located in the plurality of implantable medical devices, generating uplink telemetry transmissions to and receiving downlink telemetry transmissions from the external medical device, the transceiver transmitting a second signal in response to the first signal, wherein the external medical device selects a desired implantable medical device from the plurality of implantable medical devices based on the second signal, and initiates a telemetry session with the selected implantable medical device subsequent to selecting the desired implantable medical device, and wherein the selected implantable medical device generates a third signal enabling the external medical device to verify that the telemetry session has been initiated by the external medical device with the selected implantable medical device.

2. The medical device system of claim 1, further comprising switching means located within the selected implantable medical device, wherein the third signal is generated in response to external activation of the switching means.

3. The medical device system of claim 1, further comprising an activity circuit located within the selected implantable medical device, wherein the third signal is generated by the activity circuit in response to a signal generated external to the selected implantable medical device.

4. The medical device system of claim 1, wherein the external medical device highlights the second signal corresponding to the selected implantable medical device in response to receiving the third signal.

5. The medical device system of claim 4, wherein the highlighted second signal includes identifying information utilized by the external medical device in subsequent telemetry transmissions to the selected implantable medical device to assure that only the selected implantable medical device receives and responds to the subsequent transmissions from the external medical device.

6. The medical device system of claim 1, further comprising:
a display screen located at the external medical device displaying the uplink telemetry transmissions; and
an activity circuit located within the selected implantable medical device, wherein the third signal is generated by the activity circuit in response to a fourth signal generated external to the selected implantable medical device, and wherein an operator of the external medical device observes the generation of the fourth signal and a display of the third signal on the display screen to verify that the telemetry session has been initiated by the external medical device with the selected implantable medical device.

7. The medical device system of claim 1, wherein the initiation of the telemetry session with the selected implantable medical device by the external medical device subsequent to selecting the desired implantable medical device includes generation of a patient stimuli by the selected implantable medical device, detectable by one or both of a patient corresponding to the selected implantable medical device and an operator of the external medical device, to provide notice of the initiated telemetry session.

8. The medical device system of claim 7, wherein the patient stimuli includes one of an audible signal, a vibration, a pacing shift rate, and a pacing burst.

9. The medical device system of claim 1, wherein the initiated telemetry session is terminated in response to the third signal not being generated within a predetermined time period.

10. A medical device system, comprising:
an external medical device generating downlink telemetry transmissions to and receiving uplink telemetry transmissions from a plurality of implantable medical devices, the external medical device simultaneously transmitting a first signal to a plurality of implantable medical devices; and
a transceiver, located in the plurality of implantable medical devices, generating uplink telemetry transmissions to and receiving downlink telemetry transmissions from the external medical device, the transceiver transmitting a second signal in response to the first signal, wherein the external medical device selects a desired implantable medical device from the plurality of implantable medical devices based on the second signal, and initiates a telemetry session with the selected implantable medical device subsequent to selecting the desired implantable medical device, and wherein an operator of the external medical device requests generation of a third signal by the selected implantable medical device enabling the external medical device to verify that the telemetry session has been initiated by the external medical device with the selected implantable medical device and the initiated telemetry session is terminated in response to the third signal not being generated within a predetermined time period.

11. The medical device system of claim 10, further comprising switching means located within the selected implantable medical device, wherein the third signal is generated in response to external activation of the switching means.

12. The medical device system of claim 10, further comprising an activity circuit located within the selected implantable medical device, wherein the third signal is generated by the activity circuit in response to a fourth signal generated external to the selected implantable medical device.

13. The medical device system of claim 10, wherein the external medical device highlights the second signal corresponding to the selected implantable medical device in response to receiving the third signal.

14. The medical device system of claim 13, wherein the highlighted second signal includes identifying information utilized by the external medical device in subsequent telemetry transmissions to the selected implantable medical device to assure that only the selected implantable medical device receives and responds to the subsequent transmissions from the external medical device.

15. The medical device system of claim 10, further comprising:

a display screen located at the external medical device displaying the uplink telemetry transmissions; and
an activity circuit located within the selected implantable medical device, wherein the third signal is generated by the activity circuit in response to a fourth signal generated external to the selected implantable medical device, and wherein an operator of the external medical device observes the generation of the fourth signal and a display of the third signal on the display screen to verify that the telemetry session has been initiated by the external medical device with the selected implantable medical device.

16. The medical device system of claim 10, wherein the initiation of the telemetry session with the selected implantable medical device by the external medical device subsequent to selecting the desired implantable medical device includes generation of a patient stimuli by the selected implantable medical device, detectable by one or both of the operator and a patient corresponding to the selected implantable medical device, to provide notice of the initiated telemetry session.

17. The medical device system of claim 16, wherein the patient stimuli includes one of an audible signal, a vibration, a pacing shift rate, and a pacing burst.

18. A medical device system, comprising:
an external medical device generating downlink telemetry transmissions to and receiving uplink telemetry transmissions from a plurality of implantable medical devices, the external medical device simultaneously transmitting a first signal to a plurality of implantable medical devices; and
a transceiver, located in the plurality of implantable medical devices, generating uplink telemetry transmissions to and receiving downlink telemetry transmissions from the external medical device, the transceiver transmitting a second signal in response to the first signal, the external medical device selecting the desired implantable medical device from the plurality of implantable medical devices based on the second signal, and initiating a telemetry session with the selected implantable medical device subsequent to selecting the desired implantable medical device;
a display screen located at the external medical device displaying the uplink telemetry transmissions; and
an activity circuit generating a third signal transmitted to the external medical device through the transceiver corresponding to the selected implantable medical device in response to a fourth signal generated external to the selected implantable medical device, and wherein an operator of the external medical device observes the generation of the fourth signal and a display of the third signal on the display screen to verify that the telemetry session has been initiated by the external medical device with the selected implantable medical device.

19. The medical device system of claim 18, wherein the external medical device highlights the second signal corresponding to the selected implantable medical device in response to receiving the third signal.

20. The medical device system of claim 19, wherein the highlighted second signal includes identifying information utilized by the external medical device in subsequent telemetry transmissions to the selected implantable medical device to assure that only the selected implantable medical device receives and responds to the subsequent transmissions from the external medical device.

21. The medical device system of claim 20, wherein the initiation of the telemetry session with the selected implantable medical device by the external medical device subsequent to selecting the desired implantable medical device includes generation of a patient stimuli by the selected implantable medical device, detectable by one or more of the operator, the external medical device through the selected implantable medical device, and a patient corresponding to the selected implantable medical device, to provide notice of the initiated telemetry session.

22. The medical device system of claim 21, wherein the patient stimuli includes one of an audible signal, a vibration, a pacing shift rate, and a pacing burst.

23. The medical device system of claim 22, wherein the initiated telemetry session is terminated in response to the third signal not being generated within a predetermined time period.

24. A method of verifying that a telemetry session has been initiated by an external medical device with a desired implantable medical device of a plurality of implantable medical devices, comprising the steps of:

transmitting a first signal from the external medical device;

transmitting a second signal from the plurality of implantable medical devices to the external medical device in response to the first signal;

selecting an implantable medical device from the plurality of implantable medical devices in response to the second signal;

initiating a telemetry session with the selected implantable medical device; and generating a third signal transmitted to the external medical device from the selected implantable device enabling the external medical device to verify that the telemetry session has been initiated with the selected implantable medical device, wherein the third signal is generated in response to a signal generated external to the selected implantable medical device.

25. The method of claim 24, further comprising the step of highlighting a display of the second signal corresponding to the selected implantable medical device in response to the third signal.

26. The method of claim 25, wherein the highlighted display of the second signal includes identifying information utilized by the external medical device in subsequent telemetry transmissions to the selected implantable medical device to assure that only the selected implantable medical device receives and responds to the subsequent transmissions from the external medical device.

27. The method of claim 26, wherein the third signal is generated in response to a fourth signal generated external to the selected implantable medical device, and wherein an operator of the external medical device observes the generation of the fourth signal and a display of the third signal to verify that the telemetry session has been initiated by the external medical device with the selected implantable medical device.

28. The method of claim 27, wherein the step of initiation a telemetry session includes generating a patient stimuli, detectable by one or more of the external medical device through the selected implantable medical device, a patient corresponding to the selected implantable medical device, and an operator of the external medical device, to provide notice of the initiated telemetry session.

29. The medical device system of claim 28, wherein the patient stimuli includes one of an audible signal, a vibration, a pacing shift rate, and a pacing burst.

* * * * *